(12) United States Patent
Davis et al.

(10) Patent No.: US 7,704,935 B1
(45) Date of Patent: Apr. 27, 2010

(54) CHLORHEXIDINE ACETATE ANTISEPTIC CLEANING AGENT

(75) Inventors: Bryan G. Davis, Sandy, UT (US); Minh Q. Hoang, Sandy, UT (US); Mohammad A. Khan, Sandy, UT (US); Donald E. Hunt, Mapleton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/349,347

(22) Filed: Jan. 6, 2009

(51) Int. Cl.
*C11D 3/48* (2006.01)
*C11D 3/44* (2006.01)

(52) U.S. Cl. .................. 510/131; 510/130; 510/157; 510/161; 510/382; 510/386; 510/387; 510/388; 510/407; 510/432

(58) Field of Classification Search .......... 510/157, 510/161, 407, 432, 382, 386, 387, 388, 130, 510/131
See application file for complete search history.

(56) References Cited

U.S. PATENT DOCUMENTS

| | | | |
|---|---|---|---|
| 4,584,192 A * | 4/1986 | Dell et al. ............... 424/78.07 |
| 4,716,032 A * | 12/1987 | Westfall et al. ............ 424/45 |
| 4,915,934 A * | 4/1990 | Tomlinson .............. 424/45 |
| 4,925,668 A | 5/1990 | Khan et al. |
| 5,023,082 A * | 6/1991 | Friedman et al. .......... 424/426 |
| 5,512,199 A * | 4/1996 | Khan et al. ............. 510/131 |
| 5,547,662 A * | 8/1996 | Khan et al. ............. 424/78.03 |
| 5,616,338 A * | 4/1997 | Fox et al. .............. 424/423 |
| 5,861,440 A * | 1/1999 | Gohla et al. ............. 514/738 |
| 6,051,609 A * | 4/2000 | Yu et al. ............... 514/557 |
| 6,337,357 B1 * | 1/2002 | Fukunishi et al. ......... 523/122 |
| 6,413,539 B1 * | 7/2002 | Shalaby ................ 424/426 |
| 6,488,942 B1 * | 12/2002 | Ingemann .............. 424/401 |
| 6,846,846 B2 | 1/2005 | Modak et al. |
| 6,861,060 B1 * | 3/2005 | Luriya et al. ............. 424/400 |
| 7,198,800 B1 * | 4/2007 | Ko .................. 424/443 |
| 7,268,165 B2 | 9/2007 | Greten et al. |
| 2001/0016589 A1 * | 8/2001 | Modak et al. ............ 514/310 |
| 2002/0144705 A1 * | 10/2002 | Brattesani et al. .......... 132/321 |
| 2003/0072781 A1 * | 4/2003 | Pelerin ................. 424/401 |
| 2003/0162839 A1 * | 8/2003 | Symington et al. ......... 514/637 |
| 2004/0039349 A1 * | 2/2004 | Modak et al. ............ 604/265 |
| 2006/0165751 A1 * | 7/2006 | Chudzik et al. ........... 424/422 |
| 2006/0239954 A1 * | 10/2006 | Sancho ................ 424/70.27 |
| 2008/0075761 A1 * | 3/2008 | Modak et al. ............ 424/443 |
| 2008/0182921 A1 * | 7/2008 | Suh et al. .............. 523/116 |

OTHER PUBLICATIONS

Gama Healthcare, Cline Alcoholic 2% Chlorhexidine, http://www.gamahealthcare.com/clinellaca2c.html, pp. 1-3, Nov. 7, 2008.
Sage Products, Inc., Preoperative Skin Preparation for the Surgical Patient, http://www.sageproducts.com/products/skin-prep.cfm, 1 page, Oct. 31, 2008.
Sage Products, Inc., Address Multi-Drug Resistant Organisms on the Skin with Early Preop Prep, http://www.sageproducts.com/products/ssi-prevention.cfm, 1 page, Oct. 31, 2008.
Sage Products, Inc., Preoperative Skin Preparation and Perioperative Oral Care for the Short-Term Ventilated Patient, http://www.sageproducts.com/products/ssi-vap-prevention.cfm, 1 page, Oct. 31, 2008.
Enturia, ChloraPrep, http://www.enturia.com/products/chloraPrep/chloraPrep-product.html, pp. 1-3, Oct. 31, 2008.

* cited by examiner

*Primary Examiner*—Charles I Boyer
(74) *Attorney, Agent, or Firm*—Mony R. Ghose; Craig Metcalf; Kirton & McConkie

(57) ABSTRACT

An antiseptic cleaning agent, generally, comprising chlorhexidine acetate and a solvent, such as an alcohol and/or water. The chlorhexidine acetate acts as a highly effective biocide. Additionally, the chlorhexidine acetate allows the cleaning agent to dry without leaving a tacky residue. Where the cleaning agent comprises one or more alcohols, the alcohols may comprise any suitable alcohols, including lower alcohols having from 1 to 6 carbon atoms, such as ethanol and isopropanol. In addition to chlorhexidine acetate, the cleaning agent optionally comprises another non-alcohol biocide, such as triclosan. The cleaning agent can be used in any suitable manner. For instance, the cleaning agent may be impregnated in an absorbent material, such as a towelette, swabstick, or gauze. Additionally, the absorbent material may comprise a positively charged or a non-ionic substance, such as polypropylene or polyester.

7 Claims, 2 Drawing Sheets

_US 7,704,935 B1_

CHLORHEXIDINE ACETATE ANTISEPTIC CLEANING AGENT

BACKGROUND OF THE INVENTION

This disclosure relates generally to antiseptic cleaning agents. In particular, this disclosure discusses an antiseptic cleaning agent comprising chlorhexidine acetate. Moreover, this disclosure discusses methods and apparatus associated with the chlorhexidine antiseptic cleaning agent.

In the fields of medicine and health care, a patient's skin may be punctured in a variety of manners and for a variety of reasons. In one example, a patient's skin is cut with a sharp object, such as a scalpel, for surgical reasons. In another example, a cannula or an intravenous ("IV") catheter is forced through the patient's skin into an interior space, such as the patient's vasculature. In this example, the cannula or IV catheter can be used for infusing fluid (e.g., saline solution, medicaments, and/or total parenteral nutrition) into the patient, withdrawing fluids (e.g., blood) from the patient, and/or monitoring various parameters of the patient's vascular system.

However, when a patient's skin is punctured, the likelihood of infection in the patient increases. Indeed, it is estimated that each year hundreds of thousands of patients in the United States alone develop some form of bloodstream infection that is caused by pathogens that were communicated to the patient through or because of an IV catheter or another IV access device, such as a hypodermic needle. Many of the bacterial pathogens that cause these catheter-related bloodstream infections are common skin colonizers, or flora that exist on the patient's skin, and are often believed to enter the patient's body through the catheter insertion site.

Often, these catheter-related bloodstream infections cause patient illness and, in some cases, death. Furthermore, because some infections are caused by bacterial strains (e.g., Methicillin-resistant _Staphylococcus aureus_ ("MRSA") and Vancomycin-resistant _Enterococci_ ("VRE")) that are resistant to antibiotics, such infections can be hard to treat and may be becoming more prevalent. Additionally, because patients that have a bloodstream infection may require additional medical treatment, catheter-related bloodstream infections may also be associated with increased medical costs.

In an attempt to limit bloodstream infections (i.e., catheter-related infections) in hospital, outpatient, home care, and other health care settings, many have implemented sanitary techniques. For example, many health care providers have placed a strong emphasis on wearing gloves, cleaning hands, cleaning the insertion site on patient's skin before the catheter or other sharp medical device punctures the skin, cleaning the catheter site after the puncture, and using sterilize medical instruments.

While hands, skin, medical instruments, and other surfaces in health care settings are cleaned in a variety of methods, often cleansers with one or more antimicrobial agents are used to clean such surfaces. However, such cleansers are not without their shortcomings. For example, many cleansers are ineffective against some common types of microbes. For instance, as mentioned above, some pathogens, such as MRSA and VRE, have developed a resistance to certain antimicrobial agents.

In another example, when certain cleansers dry, the cleansers leave a tacky residue on the surfaces to which the cleansers were applied. Accordingly, such cleansers may cause several challenges. For instance, some cleansers, such as those containing chlorhexidine gluconate, dry to leave a tacky residue. Accordingly, such cleansers can adversely impact the adhesion of dressings, wound closure tapes, and bandages. In other instances, the tacky residue of such cleansers may be uncomfortable on a patient's skin. In still other instances, the tacky residue of such cleansers can catch and hold pathogens, dirt, fibers, and other debris. In yet other instances, the tacky residue can adversely impact devices that are cleaned with it. For example, when a cleanser that leaves a tacky residue is used to a clean surface that is configured to move across another surface (e.g., as is the case with scissor blades, catheter valve surfaces, catheter connectors, and many other medical devices), the cleanser's tacky residue may adversely impact the movement of one surface across another. For example, where a catheter connector has been cleaned with a cleanser that dries to leave a tacky residue, a person may find it difficult to twist the connector onto a mating connector. It should further be noted that the problems associated with cleansers that dry to leave a tacky residue may become worse where the cleansers are used multiple times in the same area so as to cause a build-up of the tacky residue.

The present disclosure discusses an antiseptic cleaning agent comprising chlorhexidine acetate. Generally, this chlorhexidine acetate cleaning agent is effective against a wide range of pathogens and does not leave a tacky residue when it dries.

BRIEF SUMMARY OF THE INVENTION

The present application relates to an antiseptic cleaning agent. While the cleaning agent may comprise any suitable ingredient, it typically comprises chlorhexidine acetate and a solvent that is capable of dissolving the chlorhexidine acetate. Generally, the cleaning agent is effective at killing or preventing/impeding pathogen growth. Additionally, instead of leaving a tacky residue, like certain cleansers comprising chlorhexidine gluconate, the described cleaning agent leaves a non-tacky salt residue of the chlorhexidine acetate.

The cleaning agent may comprise any suitable amount of the chlorhexidine acetate. In some instances, chlorhexidine acetate accounts for anywhere from about 0.01% to about 10% of the cleaning agent's total weight. In other instances, chlorhexidine acetate comprises between about 0.1% and about 5% of the cleaning agent's overall weight. In still other instances, chlorhexidine acetate accounts for between about 0.5% and about 2% of the cleaning agent, by weight.

The solvent may comprise any fluid that is suitable for dissolving the chlorhexidine acetate and which is suitable for use on human skin or a medical device. Some examples of such solvents may comprise alcohol, water, polypropylene glycol, polyol glycol, poloxamer, glycerin, and combinations thereof. However, in some presently preferred implementations, the solvent comprises a fluid, such as alcohol or water, which readily evaporates and which does not leave a tacky residue upon evaporation.

Where the solvent comprises an alcohol, the solvent may comprise any suitable alcohol, including a lower alcohol with between 1 and 6 carbons (e.g., methanol, ethanol, isopropanol, etc.). Additionally, the solvent may comprise any number of alcohols. Indeed, in some preferred embodiments, the solvent comprises isopropanol or both isopropanol and ethanol.

The cleaning agent may comprise any suitable amount of alcohol. Indeed, in some instances, the cleaning agent comprises at least 40% alcohol, by weight. In other instances, the cleaning agent comprises between about 40% and about 99% alcohol, by weight (e.g., about 95%±4.5%). In still other instances, the cleaning agent comprises between about 60% and about 80% (e.g., about 70%±5%) of the cleaning agent's overall weight.

In addition to, or in place of, the alcohol, the cleaning agent may also comprise water. The water may be provided to the cleaning agent in any suitable manner. For instance, the water may be added to the cleaning agent in the form of an aqueous solution or as purified water. Additionally, the cleaning agent may comprise any suitable amount of water. In some implementations, water accounts for between about 1% and about 99% (e.g., about 98% water) of the cleaning agent, by weight. In other implementations, water accounts for between about 20% and about 40% of the cleaning agent, by weight. In still other embodiments, water accounts for between about 25% and about 30% of the cleaning agent, by weight.

In some instances, in addition to the chlorhexidine acetate, the cleaning agent comprises a second biocidal agent. The second biocidal agent may comprise any chemical, besides alcohol, that is capable of reducing pathogens on a surface and which allows the cleaning agent to function as intended. One example of such a second biocidal agent comprises triclosan.

Where the cleaning agent comprises a second biocidal agent, the cleaning agent may comprise any suitable amount of the second biocidal agent. Indeed, in some implementations, the second biocidal agent (e.g., triclosan) accounts for between about 0.01% and about 10% of the cleaning agent, by weight. In other implementations, the second biocidal agent comprises between about 0.1% and about 5% of the cleaning agent's total weight. In still other implementations, the second biocidal agent comprises between about 0.5% and about 2% of the cleaning agent.

In addition to the aforementioned ingredients, the cleaning agent may comprise any other ingredient that allows the biocidal agent to disinfect surfaces while maintaining its ability to dry without leaving a tacky residue. By way of example, the cleaning agent may comprise one or more known or novel detackifying agents, thickening agents, neutralizing agents, pH adjusters, metallic salts, dyes, fragrances, and/or other suitable chemicals.

The cleaning agent may be used in any suitable manner. For example, the cleaning agent can be disposed in and/or on a receptacle that is capable of dispensing the cleaning agent. Some examples of suitable receptacles comprise an absorbent material, a spray bottle, and an aerosol can. Furthermore, some examples of suitable absorbent materials comprise a towelette, a swabstick, gauze, fabric, a wad or mesh of fibers, and/or any other suitable substance that is capable of absorbing the cleaning agent and dispensing some of the cleaning agent when the substance contacts a surface.

Where the cleaning agent is disposed in and/or on an absorbent material, the material may comprise any suitable substance, including, but not limited to, a form of cellulose (e.g., cotton, paper, etc.), polyester, polypropylene, polyurethane, foam, silicone, etc. However, chlorhexidine acetate, which may be cationic, can bind to negatively charged substances (e.g., cotton, paper, etc.) and, thereby, reduce the active shelf live and the amount of chlorhexidine acetate that is released from the absorbent material. Accordingly, in some presently preferred embodiments, the absorbent material comprises a cationic and/or non-ionic substance. For instance, the absorbent material may substantially comprise polyester, polypropylene, cationic surfactant coated cotton, silicone, and/or another similar material.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof, which are depicted in the appended Figures. Understanding that these Figures depict only typical embodiments of the invention and are not, therefore, to be considered to be limiting of its scope, the invention will be described and explained with additional specificity and detail through the use of the accompanying Figures in which.

DETAILED DESCRIPTION OF THE INVENTION

Figure 1:
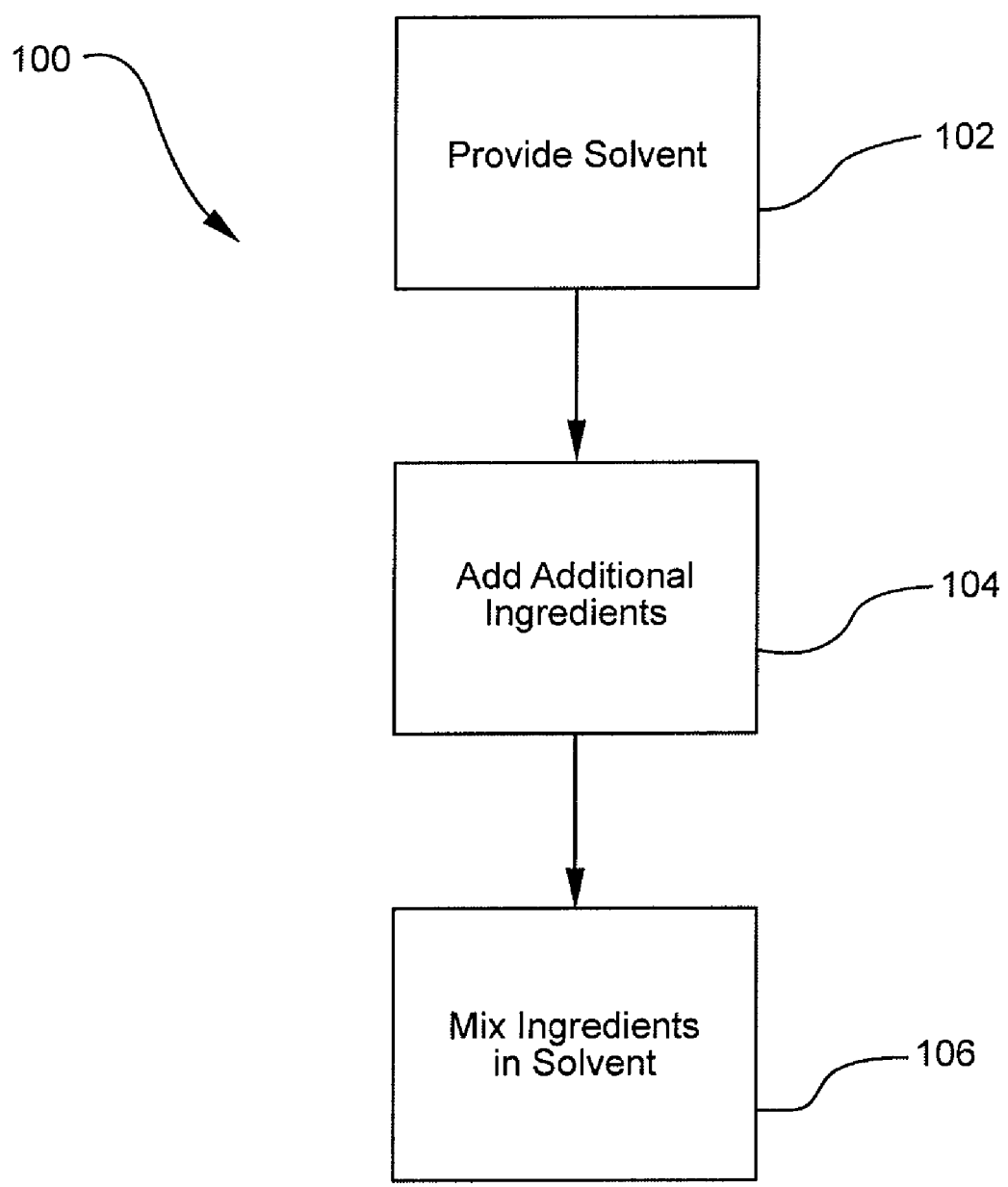
FIG. 1 illustrates flow chart of a representative method for making the chlorhexidine acetate cleaning agent.

In order to provide a thorough understanding of the invention, the following description discusses specific details. The skilled artisan, however, would understand that the invention can be practiced without employing these specific details. Indeed, the invention can be modified in any suitable manner and can be used in conjunction with any suitable chemical, apparatus, and technique conventionally used in the industry. Thus, the following more detailed description of the embodiments of the invention is not intended to be limiting in scope, but is merely representative of some presently preferred embodiments. Additionally, while the following discussion focuses on using the invention in health care settings, the cleaning agent may be used in any suitable setting.

Generally, this application discusses an antiseptic cleaning agent that is effective at killing and preventing the growth of a wide range of pathogens. As used herein the terms pathogen and pathogens may include any potentially infectious microorganism, bacteria (e.g., undulating bacteria, gram-negative bacteria, gram-positive bacteria, aerobic bacteria, anaerobic bacteria, mycobacteria, spriochetes, *Staphylococcus epidermis, Staphylococcus aureus, Escerchia coli, Proteus vulgaris, Streptococcus faecalis, Klebsiella, Enterobacter aerogenes, Proteus mirabilis*, and the like), fungi (e.g., fungal spores, *Aspergillus niger, Aspergillus flavus, Rhizopus nigricans, Cladosporium herbarium, Epidermophyton Floccosum, Trichophyton mentagrophytes, Histoplasma capsulatum*, and the like), yeasts (e.g., *Saccharomyces cerevisiae, Candida albicans*, and the like), virus, and/or other potentially hazardous microbes. Additionally, in some presently preferred embodiments, the described antiseptic cleaning agent preferably dries without leaving a tacky residue. As used herein, the term tacky residue may connote a gummy, sticky, adhesive, and/or gluey deposit.

The antiseptic cleaning agent may comprise any suitable ingredient that allows it to kill a wide range of pathogens, dry without leaving a tacky residue, and be suitable for dermal use on humans and/or use on medical devices. In some embodiments, however, the cleaning agent comprises a first biocidal agent and one or more solvents that are capable of dissolving the first biocidal agent. To provide a better understanding of the cleaning agent, the first biocidal agent and the solvent are described below in more detail.

The first biocidal agent may comprise any chemical, besides alcohol, that is suitable for use on human skin, dries without leaving a tacky residue, and which kills and/or inhibits/prevents the propagation of potentially infectious pathogens. In some embodiments, the first biocidal agent comprises a salt of chlorhexidine, such as chlorhexidine acetate, which may also be referred to as chlorhexidine diacetate or $C_{26}H_{38}Cl_2N_{10}O_4$.

Chlorhexidine acetate may have several characteristics that allow it to be an effective biocidal agent. In one example, chlorhexidine acetate is effective at killing and inhibiting the growth of a wide variety of pathogens that are common to healthcare settings. In another example, when chlorhexidine acetate in the cleaning agent dries, the chlorhexidine acetate forms a non-tacky deposit (e.g., a salt) on the surface to which it was applied. This powder residue may remain on the surface for a period of time and, thereby, provide the surface with a residual biocidal effect.

The cleaning agent may comprise any suitable concentration of chlorhexidine acetate that allows the cleaning agent to effectively kill or prevent pathogen proliferation while being safe for use on human skin. In some embodiments, the chlorhexidine acetate comprises from about 0.01% to about 10% of the total weight of the cleaning agent (i.e., between about 5% and about 10%). In other embodiments, the chlorhexidine acetate comprises from about 0.1% to about 5% of the cleaning agent, by weight. In still other embodiments, the chlorhexidine acetate comprises from about 0.5% to about 2% of the cleaning agent, by weight.

As an illustration of some suitable concentrations of chlorhexidine acetate in the cleaning agent, Table 1 (shown below) contains the formulas of 12 representative formulations of the cleaning agent and states the chlorhexidine acetate concentration in each formulation.

sure). Additionally, in some presently preferred embodiments, the solvent does not dry to leave a tacky residue. Examples of such solvents may include alcohol and/or water.

Indeed, in some embodiments, the solvent comprises one or more alcohols. In addition to acting as a solvent, the alcohol(s) may have several other advantageous characteristics. For example, the alcohol may further increase the effectiveness of the cleaning agent by acting as a biocidal agent that kills at least some of the pathogens it contacts. In another example, the alcohol evaporates relatively quickly without leaving a tacky residue.

While the solvent can comprise any alcohol that is capable of dissolving chlorhexidine acetate and which is suitable for dermal application, in some embodiments, the alcohol comprises a lower alcohol having from 1 to 6 carbon atoms. Some examples of such alcohols include methanol, ethanol, n-propanol, isopropanol, butanol, pentanol, hexanol, and so forth. In some presently preferred embodiments, however, the alcohol is selected from isopropanol and ethanol.

In some embodiments, the solvent comprises more than one type of alcohol. In such embodiments, the cleaning agent may comprise any suitable number of alcohols, including 2, 3, 4, or more alcohols. Additionally, the solvent may comprise any suitable combination of alcohols. In one example, the solvent comprises isopropanol, butanol, and ethanol. In another example, the solvent comprises isopropanol and ethanol.

Where the solvent comprises more than one alcohol, the various alcohols may be present in the cleaning agent in any suitable ratio with respect to each other. For instance, in some embodiments where the cleaning agent comprises two alcohols (e.g., isopropanol and ethanol), the ratio of the first alcohol (e.g., isopropanol) to the second alcohol (e.g., ethanol) is from about 1:10 to about 1:1. In other embodiments, the ratio of the first alcohol (e.g., isopropanol) to the second alcohol (e.g., ethanol) is from about 1:3 to about 1:1. In still

TABLE 1

| Formula | 1 | 2 | 3 | 4 | 5 | 6 | 7 | 8 | 9 | 10 | 11 | 12 |
|---|---|---|---|---|---|---|---|---|---|---|---|---|
| Ethanol | 70% | 0% | 70% | 0% | 70% | 0% | 70% | 0% | 70% | 0% | 0% | 40% |
| Isopropanol | 0% | 70% | 0% | 70% | 0% | 70% | 0% | 70% | 0% | 70% | 0% | 30% |
| Chlorhexidine Diacetate | 1% | 1% | 2% | 2% | 3% | 3% | 4% | 4% | 4% | 4% | 2% | 2% |
| Water | 29% | 29% | 28% | 28% | 27% | 27% | 26% | 26% | 26% | 26% | 98% | 28% |

For instance, Table 1 shows that in formulations 1 and 2, chlorhexidine acetate comprises about 1% of the cleaning agent's total weight. Similarly, Table 1 shows that in formulations 3, 4, 11, and 12, chlorhexidine acetate comprises about 2% of the cleaning agent's total weight. Table 1 further shows that in formulations 5 and 6, chlorhexidine acetate comprises about 3% of the cleaning agent, by weight. Finally, Table 1 shows that in formulations 7, 8, 9, and 10, chlorhexidine acetate comprises about 4% of the cleaning agent's total weight.

As mentioned, the cleaning agent also comprises a solvent. The solvent may comprise virtually any fluid that is capable of dissolving chlorhexidine acetate and which is suitable for dermal use. Some examples of such solvents may comprise alcohol, water, glycol, polypropylene glycol, polyol glycol, poloxamer, glycerin, and combinations thereof. Nevertheless, in some presently preferred embodiments, the solvent comprises a liquid that readily evaporates at room temperature and 1 atmosphere (e.g., has a relatively high vapor presother embodiments, the ratio of the first alcohol (e.g., isopropanol) to the second alcohol (e.g., ethanol) is about 1:1.4±0.2. By way of example, formula 12 in Table 1 (shown above) illustrates a formulation in which the ratio of isopropanol to ethanol is about 1:1.33.

Where the solvent in the cleaning agent comprises at least one alcohol, the cleaning agent may comprise any suitable amount of alcohol. In one example, one or more alcohols comprise at least 40% of the cleaning agent's total weight. In another example, alcohol comprises from about 40% to about 99% of the cleaning agent, by weight. In still another example, alcohol comprises from more than about 9% to about 99% of the cleaning agent. In yet another example, alcohol comprises from about 60% to about 80% of the cleaning agent, by weight. Indeed, in some presently preferred embodiments, one or more alcohols (e.g., ethanol and isopropanol) account for about 70%±5% of the cleaning agent's overall weight.

As mentioned above, in some embodiments, the solvent comprises water. In such embodiments, the water may be provided to the cleaning agent in any suitable aqueous solution, including a dilute alcohol or other solution containing water. Nevertheless, in some embodiments, the water comprises purified water, such as United States Pharacopeia ("USP") water or de-ionized water.

Where the cleaning agent comprises water, the cleaning agent may comprise any suitable amount of water. Indeed, in some embodiments, in addition to the chlorhexidine acetate, alcohol, and/or any other suitable ingredient, the remaining portion of the cleaning agent comprises water. In one example, the cleaning agent comprises from about 1% to about 99% water. For instance, water may account for more than 90% of the cleaning agent. By way of illustration, representative formula 11 in Table 1 (above) comprises about 98% water. In another example, however, about 20% to about 40% the cleaning agent's overall weight is water. In still another example, the cleaning agent comprises from about 25% to about 30% water, by weight. For instance, Table 1 shows that in formulations 1 through 10 and in formulation 12, water accounts for between about 26% and about 29% of the total cleaning agent's total weight.

In some embodiments, the cleaning agent optionally comprises at least one other non-alcohol biocidal agent ("second biocidal agent"). In such embodiments, the second biocidal agent can comprise any suitable chemical or chemicals that kill, reduce, or otherwise impede pathogen proliferation while allowing the cleaning agent to sanitize surfaces, dry without leaving a tacky residue, and be suitable for use on human skin. Some examples of suitable second biocidal agents include triclosan (5-chloro-2-(2,4-dichlorophenoxy) phenol)), silver and/or copper ions and nanoparticles (e.g., tinosan silver dihydrogen citrate), silver sulphadiazine, an imidozole, a triazole, an allyamine, phenol, hexachlorophene, an antibiotic, a sulfonamide, etc. In some presently preferred embodiments, however, the second antimicrobial agent comprises triclosan.

Where the cleaning agent comprises a second biocidal agent, the cleaning agent may comprise any suitable portion of the second biocidal agent. In one example, a second biocidal agent (e.g., triclosan) comprises from about 0.01% to about 10% of the total weight of the cleaning agent. In another example, the second biocidal agent comprises from about 0.1% to about 5% of the cleaning agent, by weight. In still another example, the second biocidal agent comprises from about 0.5% to about 2% of the cleaning agent, by weight.

In addition to the aforementioned ingredients, the cleaning agent may comprise any suitable ingredient, at any suitable concentration, which allows the cleaning agent to sanitize surfaces, be suitable for dermal use, and to dry without leaving a tacky residue. Some examples of such optional ingredients may comprise one or more known or novel detackifying agents, thickening agents, neutralizing agents, pH adjusters, metallic salts, dyes, fragrances, and/or other suitable chemicals.

The cleaning agent can also be modified to have any suitable characteristic. For example, while in some presently preferred embodiments, the cleaning agent comprises a liquid, in other embodiments, the cleaning agent can be modified to be a gel, a cream, a foam, or another fluid having a desired consistency/viscosity.

The cleaning agent may also be made in any suitable manner. For instance, FIG. 1 illustrates a representative embodiment of a method for making the cleaning agent. Specifically, at 102, FIG. 1 shows that the method 100 begins by providing a solvent. For instance, the method 100 may begin by providing an alcohol, such as isopropanol and/or ethanol, and mixing the alcohol with water, if included. At 104, FIG. 1 shows the method 100 continues by adding the additional ingredients (e.g., the chlorhexidine acetate, triclosan, pH modifiers, etc.) to the solvent (e.g., the aqueous alcohol solution), in any suitable order. Next, at 106, FIG. 1 shows the cleaning agent is further mixed until the soluble ingredients (e.g., the chlorhexidine acetate) are dissolved within the cleaning agent.

Figure 2:
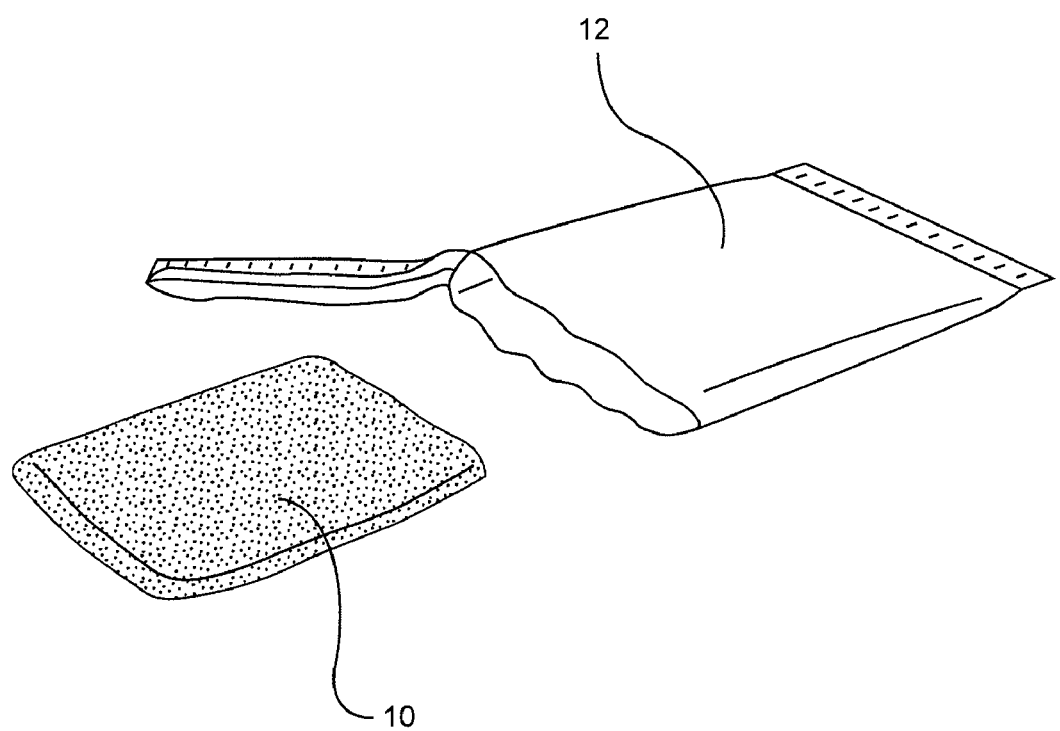
FIG. 2 illustrates a representative embodiment of a moist towelette comprising the chlorhexidine acetate cleaning agent.

The cleaning agent may be used in any suitable manner. For instance, the cleaning agent may be disposed on and/or in a receptacle, from which the agent may be dispensed or otherwise used to clean an object. In such instances, the cleaning agent may be disposed on and/or in any suitable receptacle with any component or characteristic that allows it to be used with the cleaning agent while allowing the cleaning agent to act as intended. Some examples of suitable receptacles may include an absorbent material (e.g., a towelette, gauze, a swab, a swabstick, a sponge, a sponge with a feeding-fluid reservoir applicator, a fabric, a wad of fibers, etc.), a spray bottle, an aerosol dispenser, or any other suitable container. By way of example, FIG. 2 shows a representative embodiment in which an absorbent material, namely a towelette 10, is moistened by the cleaning agent (not shown). In this example, the absorbent material may have any suitable characteristic. For instance, FIG. 2 shows the towelette 10 may be individually packaged in a wrapper 12 (e.g. a foil and paper wrapper).

Where the cleaning agent is disposed on and/or in an absorbent material, the material may comprise any suitable substance that is capable of absorbing the cleaning agent, releasing some of the agent when the absorbent material contacts (e.g., wipes) a surface, and which is suitable for use on human skin. Some examples of suitable substances may comprise cotton, paper, cellulose, wool, polyester, polypropylene, fabric, or another material that is capable of forming an absorbent object capable of applying the cleaning agent to a surface.

However, because cotton, paper, cellulose, and other similar materials can have a negative charge, the shelf life of the cationic chlorhexidine acetate in the cleaning agent may be reduced by such materials. Additionally, the cationic chlorhexidine acetate may bind to such negatively-charged materials and reduce the amount of chlorhexidine acetate that is released on a surface as the absorbent material contacts the surface. Thus, according to some preferred embodiments, the absorbent material (e.g., towelette 10) comprises a substance that has a positive charge or no charge at all. While the absorbent material may comprise any suitable cationic or non-cationic substance, some examples of such substances comprise polyester, polypropylene, cationic surfactant coated cotton, silicone, and/or another similar material.

Where the absorbent material comprises one or more substances with a positive charge or no charge at all (e.g., polyester and/or polypropylene), the absorbent material may comprise any suitable amount of such substances. For instance, in some embodiments, between about 1% and about 100% of the absorbent material comprise a substance that has a positive charge or no charge. In other embodiments, more than about 50% of the absorbent material comprises a substance that has either a positive charge or a negative charge. In still other embodiments, more than about 70% of the absorbent material comprises a substance that has either a positive charge or a negative charge. In yet other embodiments, however, about 100% of the absorbent material comprises a substance with a positive charge or no charge at all.

Because an absorbent material with no charge or a positive charge may not ionically bind to the cationic chlorhexidine acetate, the use of such an absorbent material may increase the shelf life of the chlorhexidine acetate. Additionally, because a cationic or non-ionic substance may not bind to the chlorhexidine acetate an absorbent material comprising such a substance may release more of the chlorhexidine acetate in the cleaning agent than a comparable absorbent material that substantially comprises a substance having a negative charge (e.g., cotton). Accordingly, an absorbent material that substantially comprises a material having a positive charge or no charge at all may be disinfect more effectively than a comparable absorbent material having a negative charge.

The cleaning agent may be used to clean virtually any surface. In one example, the cleaning agent is used to cleanse skin (e.g., to sanitize hands, to clean a portion of a patient's skin before the skin is punctured, to clean and care for a patient's skin after it is punctured, etc.). In another example, the cleaning agent is used to sanitize non-living objects, such as medical instruments, floors, chairs, door handles, tables, computer keyboards, computer mice, etc.

The cleaning agent may be used to sanitize a surface in any suitable manner. For example, an object, such as a medical instrument (e.g., a catheter, a syringe, scalpel, or another object used in health care settings) can be coated with the cleaning agent. In this example, the cleaning agent may be applied to the object in any suitable manner, including by wiping (e.g., via an absorbent material), spraying, soaking, misting, immersing, or otherwise applying the cleaning agent to the object. Additionally, in this example, when an object is coated with the cleaning agent, the cleaning agent may leave a layer of chlorhexidine acetate when it dries. As stated above, such a layer of chlorhexidine acetate may remain on the object for some period of time and, thereby, act to prevent growth of bacteria and to reduce the amount of bacteria and other pathogens that will colonize the object's coated surface.

EXAMPLES

The cleaning agent has proven to be highly effective at killing or preventing the proliferation of many pathogens that commonly cause bloodstream infections. By way of example, Table 2, shown below, illustrates experimental results in which 12 pathogens (as labeled and named in Columns 1 and 2, respectively) were treated with the cleaning agent, wherein the cleaning agent contained approximately 2% chlorhexidine acetate and about 70% isopropyl alcohol.

TABLE 2

| Col. 1 Test No. | Col. 2 Challenge Microorganism (ATCC #) | Col. 3 Initial Population (CFU/mL) | Col. 4 Exposure Time | Col. 5 Post Exposure Population (CFU/mL) | Col. 6 $\text{Log}_{10}$ Reduction | Col. 7 Percent Reduction |
|---|---|---|---|---|---|---|
| 1 | Candida albicans (ATCC # 10231) | $1.00 \times 10^9$ | 15 seconds | $<1.00 \times 10^3$ | 6.0000 | 99.9999% |
| | | | 30 seconds | $<1.00 \times 10^3$ | 6.0000 | 99.9999% |
| | | | 1 minute | $<1.00 \times 10^3$ | 6.0000 | 99.9999% |
| | | | 5 minutes | $<1.00 \times 10^3$ | 6.0000 | 99.9999% |
| 2 | Enterobacter cloacae cloacae (ATCC #23355) | $1.890 \times 10^9$ | 15 seconds | $<1.00 \times 10^3$ | 6.2765 | 99.9999% |
| | | | 30 seconds | $<1.00 \times 10^3$ | 6.2765 | 99.9999% |
| | | | 1 minute | $<1.00 \times 10^3$ | 6.2765 | 99.9999% |
| | | | 5 minutes | $<1.00 \times 10^3$ | 6.2765 | 99.9999% |
| 3 | Enterococcus faecalis (ATCC #29212) | $1.7350 \times 10^9$ | 15 seconds | $<1.00 \times 10^3$ | 6.2393 | 99.9999% |
| | | | 30 seconds | $<1.00 \times 10^3$ | 6.2393 | 99.9999% |
| | | | 1 minute | $<1.00 \times 10^3$ | 6.2393 | 99.9999% |
| | | | 5 minutes | $<1.00 \times 10^3$ | 6.2393 | 99.9999% |
| 4 | Enterococcus Faecalis MDR; VRE (ATCC #25922) | $2.750 \times 10^9$ | 15 seconds | $<1.00 \times 10^3$ | 6.4393 | 99.9999% |
| | | | 30 seconds | $<1.00 \times 10^3$ | 6.4393 | 99.9999% |
| | | | 1 minute | $<1.00 \times 10^3$ | 6.4393 | 99.9999% |
| | | | 5 minutes | $<1.00 \times 10^3$ | 6.4393 | 99.9999% |
| 5 | Escherichia coli (ATCC # 25922) | $7.750 \times 10^8$ | 15 seconds | $<1.00 \times 10^3$ | 5.8893 | 99.9999% |
| | | | 30 seconds | $<1.00 \times 10^3$ | 5.8893 | 99.9999% |
| | | | 1 minute | $<1.00 \times 10^3$ | 5.8893 | 99.9999% |
| | | | 5 minutes | $<1.00 \times 10^3$ | 5.8893 | 99.9999% |
| 6 | Klebsiella pneumoniae (ATCC # 13883) | $2.240 \times 10^9$ | 15 seconds | $<1.00 \times 10^3$ | 6.3502 | 99.9999% |
| | | | 30 seconds | $<1.00 \times 10^3$ | 6.3502 | 99.9999% |
| | | | 1 minute | $<1.00 \times 10^3$ | 6.3502 | 99.9999% |
| | | | 5 minutes | $<1.00 \times 10^3$ | 6.3502 | 99.9999% |
| 7 | Proteus hauseri (ATTCC # 13315) | $3.450 \times 10^9$ | 15 seconds | $<1.00 \times 10^3$ | 6.5378 | 99.9999% |
| | | | 30 seconds | $<1.00 \times 10^3$ | 6.5378 | 99.9999% |
| | | | 1 minute | $<1.00 \times 10^3$ | 6.5378 | 99.9999% |
| | | | 5 minutes | $<1.00 \times 10^3$ | 6.5378 | 99.9999% |
| 8 | Pseudomonas aeruginosa (ATCC # 27853) | $1.040 \times 10^9$ | 15 seconds | $<1.00 \times 10^3$ | 6.0170 | 99.9999% |
| | | | 30 seconds | $<1.00 \times 10^3$ | 6.0170 | 99.9999% |
| | | | 1 minute | $<1.00 \times 10^3$ | 6.0170 | 99.9999% |
| | | | 5 minutes | $<1.00 \times 10^3$ | 6.0170 | 99.9999% |
| 9 | Serratia marcescens (ATCC #8100) | $2.1350 \times 10^9$ | 15 seconds | $<1.00 \times 10^3$ | 6.3294 | 99.9999% |
| | | | 30 seconds | $<1.00 \times 10^3$ | 6.3294 | 99.9999% |
| | | | 1 minute | $<1.00 \times 10^3$ | 6.3294 | 99.9999% |
| | | | 5 minutes | $<1.00 \times 10^3$ | 6.3294 | 99.9999% |
| 10 | Staphylococcus aureus aureus (ATCC #25923) | $1.080 \times 10^9$ | 15 seconds | $<1.00 \times 10^3$ | 6.0334 | 99.9999% |
| | | | 30 seconds | $<1.00 \times 10^3$ | 6.0334 | 99.9999% |
| | | | 1 minute | $<1.00 \times 10^3$ | 6.0334 | 99.9999% |
| | | | 5 minutes | $<1.00 \times 10^3$ | 6.0334 | 99.9999% |
| 11 | Staphylococcus aureus aureus | $3.0750 \times 10^9$ | 15 seconds | $<1.00 \times 10^3$ | 6.4878 | 99.9999% |
| | | | 30 seconds | $<1.00 \times 10^3$ | 6.4878 | 99.9999% |
| | | | 1 minute | $<1.00 \times 10^3$ | 6.4878 | 99.9999% |
| | | | 5 minutes | $<1.00 \times 10^3$ | 6.4878 | 99.9999% |

TABLE 2-continued

| Col. 1 Test No. | Col. 2 Challenge Microorganism (ATCC #) | Col. 3 Initial Population (CFU/mL) | Col. 4 Exposure Time | Col. 5 Post Exposure Population (CFU/mL) | Col. 6 $Log_{10}$ Reduction | Col. 7 Percent Reduction |
|---|---|---|---|---|---|---|
| 12 | Staphylococcus aureus VRSA (BSLI #062707NARSAVRsal) | $1.4450 \times 10^9$ | 15 seconds | $<1.00 \times 10^3$ | 4.1754 | 99.9933% |
|  |  |  | 30 seconds | $<1.00 \times 10^3$ | 4.1754 | 99.9987% |
|  |  |  | 1 minute | $<1.00 \times 10^3$ | 4.1754 | 99.9999% |
|  |  |  | 5 minutes | $<1.00 \times 10^3$ | 4.1754 | 99.9998% |
| 13 | Staphylococcus epidermidis (ATCC # 12228) | $6.650 \times 10^8$ | 15 seconds | $<1.00 \times 10^3$ | 5.8228 | 99.9998% |
|  |  |  | 30 seconds | $<1.00 \times 10^3$ | 5.8228 | 99.9998% |
|  |  |  | 1 minute | $<1.00 \times 10^3$ | 5.8228 | 99.9998% |
|  |  |  | 5 minutes | $<1.00 \times 10^3$ | 5.8228 | 99.9998% |

In this experiment, the initial population size of a colony of each pathogen was calculated, as shown in column 3. Column 4 shows that each colony was treated with the cleaning agent for a period 15 seconds, 30 seconds, 1 minute, and 5 minutes. At after each period of exposure, the population and $Log_{10}$ reduction of each colony was calculated, as shown in Columns 5 and 6, respectively. Finally, Column 7 shows the percent reduction in each colony's population was calculated.

As Column 7 shows that after 15 seconds, 30 seconds, 1 minute, and 5 minutes, the cleaning agent reduced the population size of the colonies of *Candida albicans* (Test No. 1), *Enterbacter cloacae cloacae* (Test No. 2), *Enterococcus faecalis* (Test No. 3), multi-drug resistant ("MDR") *Enterococcus Faecalis*/VRE *Enterococcus Faecalis* (Test No. 4), *Escherchia coli* (Test No. 5), *Klebsiella pneumonia* pneumonia (Test No. 6), *Proteus hauseri* (Test No. 7), *Pseudomonas aeruginosa* (Test No. 8), *Serratia mascarens* (Test No. 8), *Staphylococcus aureus aureus* (Test No. 10), and MRSA *Staphylococcus aureus aureus* (Test No. 11) by about 99.999%. Similarly, Column 7 shows that the cleaning agent reduced the population size of the vancomycin-resistant *Staphylococcus aureus* ("*Staphylococcus aureus* VRSA") (Test No. 12) and the *Staphylococcus epidermis* (Test No. 13) by about 99.9998% or more within about 1 minute of exposure time.

The described cleaning agent may possess several beneficial and advantageous characteristics. In one example, unlike certain prior art cleansers that comprise chlorhexidine gluconate, which dries to form a tacky residue, the chlorhexidine acetate in the described cleaning agent does not leave a tacky residue when it dries. Accordingly, devices having surfaces that are configured to rub against another surface (e.g., scissor blades, catheter connectors, catheter valves, etc.) and that are cleaned with the described cleaning agent may be subject to less friction between articulating surfaces and less device impairment than comparable devices that are cleansed with certain cleansers containing chlorhexidine gluconate. For instance, a catheter connector, such as Luer lock connector, that is cleaned with the described cleaning agent may mate more easily with a corresponding connector when the connectors are cleaned with the described cleaning agent than when the connectors are cleaned with a cleaning agent that leaves a tacky residue on the connectors' articulating surfaces. Further, because the cleaning agent does not leave a tacky residue, it does not tend to form a thick, tacky build-up when used on a surface multiple times. Accordingly, the described cleaning agent may be more suitable for repetitive use on devices, such as catheter adapters, that have surfaces that rub against each other than are certain prior art cleansers.

In another example, because the described cleaner does not leave a tacky residue, the cleaner may be more comfortable for human use as well as more aesthetically pleasing than a cleanser containing chlorhexidine gluconate or another chemical that leaves a tacky residue, which captures debris.

In still another example, because the cleaning agent may dry to leave a non-tacky chlorhexidine acetate residue on a surface, the residue may keep the surface sanitary for a longer period of time than would be possible without such a treatment. Accordingly, where the cleaning agent is used to sanitize medical instruments, the cleaning agent may reduce a patient's risk of medical-instrument related infection—especially in instances where the medical instrument is used for a prolonged time period. Additionally, because the cleaning agent may increase the period of time in which the medical instrument is sanitary, the cleaning agent may increase the useful life of the medical instrument and, thereby, further act to reduce medical costs.

The present invention may be embodied in other specific forms without departing from its structures, methods, or other essential characteristics as broadly described herein and claimed hereinafter. The described embodiments and examples are all to be considered in every respect as illustrative only, and not as being restrictive. The scope of the invention is, therefore, indicated by the appended claims, rather than by the foregoing description. All changes that come within the meaning and range of equivalency of the claims are to be embraced within their scope.

The invention claimed is:

1. An antiseptic cleaning agent, consisting essentially of:
   a) a first non-alcohol, biocidal agent comprising chlorhexidine acetate, wherein the chlorhexidine acetate comprises about 0.01% to about 10% of the cleaning agent, by weight; and
   b) more than about 90% of the cleaning agent by weight of an alcohol comprising isopropanol and ethanol, wherein a ratio of the isopropanol to ethanol is from about 1:3 to about 1:1, and wherein the cleaning agent does not leave a tacky residue when it dries.

2. The cleaning agent of claim 1, wherein the cleaning agent further comprises 5-chloro-2-(2,4-dichlorophenoxy) phenol.

3. The cleaning agent of claim 2, wherein the 5-chloro-2-(2,4-dichlorophenoxy)phenol comprises from about 0.01% to about 10% of the cleaning agent, by weight.

4. An antiseptic cleaning agent device, consisting essentially of:

a) a first non-alcohol, biocidal agent comprising chlorhexidine acetate, wherein the chlorhexidine acetate comprises about 0.01% to about 10% of the cleaning agent, by weight;

b) more than about 90% of the cleaning agent by weight of an alcohol comprising isopropanol and ethanol, wherein a ratio of the isopropanol to ethanol is from about 1:3 to about 1:1; and c) an absorbent material, wherein the absorbent material is impregnated with the cleaning agent, and wherein the cleaning agent does not leave a tacky residue when it dries.

5. The cleaning agent device of claim 4, further comprising 5-chloro-2-(2,4-dichlorophenoxy)phenol, which comprises from about 0.01% to about 10% of the cleaning agent, by weight.

6. The cleaning agent device of claim 4, wherein the absorbent material comprises at least one of a cationic and a non-ionic substance.

7. The cleaning agent device of claim 6, wherein the absorbent material is selected from at least one of a polyester, a polypropylene, a cationic surfactant coated cotton, and a silicone.

* * * * *